(12) United States Patent
Rees et al.

(10) Patent No.: US 7,395,159 B2
(45) Date of Patent: Jul. 1, 2008

(54) METHOD, SYSTEM AND DEVICES FOR CONVERTING VENOUS BLOOD VALUES TO ARTERIAL BLOOD VALUES

(75) Inventors: Stephen Edward Rees, Aalborg (DK); Steen Andreassen, Aalborg (DK)

(73) Assignee: OBI APS, Aalborg (DK)

( * ) Notice: Subject to any disclaimer, the term of this patent is extended or adjusted under 35 U.S.C. 154(b) by 204 days.

(21) Appl. No.: 10/522,251

(22) PCT Filed: Jul. 25, 2003

(86) PCT No.: PCT/DK03/00512

§ 371 (c)(1),
(2), (4) Date: Sep. 16, 2005

(87) PCT Pub. No.: WO2004/010861

PCT Pub. Date: Feb. 5, 2004

(65) Prior Publication Data

US 2006/0105319 A1     May 18, 2006

(30) Foreign Application Priority Data

Jul. 26, 2002   (DK) ................. 2002 01144

(51) Int. Cl.
*G01R 27/28* (2006.01)
(52) U.S. Cl. ............ 702/19; 702/21; 600/323; 600/364; 600/368; 436/50
(58) Field of Classification Search ........ 702/19, 702/21; 600/323, 364, 368; 436/50
See application file for complete search history.

(56) References Cited

U.S. PATENT DOCUMENTS

| | | | |
|---|---|---|---|
| 3,874,850 A | 4/1975 | Sorensen et al. | |
| 5,687,718 A | 11/1997 | Fischer et al. | |
| 6,163,715 A | 12/2000 | Reuss et al. | |
| 6,206,830 B1 | 3/2001 | Kiani-Azarbayjany et al. | |
| 6,334,065 B1 | 12/2001 | Al-Ali et al. | |
| 2002/0120185 A1 | 8/2002 | Johnson | |

FOREIGN PATENT DOCUMENTS

| | | |
|---|---|---|
| EP | 0 586 025 A2 | 3/1994 |
| WO | WO 98/25514 | 6/1998 |

(Continued)

OTHER PUBLICATIONS

Bigeleisen, Paul E., Models of Venous Admixture, The American Physiological Society, vol. 25, No. 3, Sep. 2001, pp. 159-166.*

(Continued)

*Primary Examiner*—John E. Barlow, Jr.
*Assistant Examiner*—Sujoy Kundu
(74) *Attorney, Agent, or Firm*—Foley & Lardner LLP

(57) ABSTRACT

A methodology for converting venous blood values to arterial blood values provides the advantage of obviating the need for taking arterial blood samples. The method entails (i) measuring arterial oxygenation, (ii) measuring and estimating values of venous blood acid/base status and oxygenation status of a venous blood sample, and (iii) converting the venous blood values by applying a mathematical model for deriving blood acid/base status and oxygenation status into estimated arterial blood values.

11 Claims, 5 Drawing Sheets

FOREIGN PATENT DOCUMENTS

WO          WO 00 45702 A      8/2000

OTHER PUBLICATIONS

International Search Report of PCT/DK03/00512.
S.E. Rees et al., "A Dynamic Model of Carbon Dioxide Transport in the Blood", IFAC Symposium on Modelling an Control in Biomedical Systems, Mar. 23-26, 1997, XP002258602, Warwick, England, cited in the application, p. 57-p. 62.

Stephen E. Rees et al., "Acid-base chemistry of the blood—a general model", Computer Methods and Program in Biomedicine, vol. 51, 1996, pp. 107-119, XP002258603, ISSN: 0169-2607 cited in the application the whole document.

* cited by examiner

METHOD, SYSTEM AND DEVICES FOR CONVERTING VENOUS BLOOD VALUES TO ARTERIAL BLOOD VALUES

The present invention relates to methods for converting venous blood values to arterial blood values. The invention also relates to an apparatus for performing the method and relates to uses of the apparatus, when performing the method.

BACKGROUND OF THE INVENTION

The assessment of acutely ill patients is a complex process involving evaluation of the patients numerous physiological systems, e.g. the pulmonary, metabolic, renal and circulatory systems. Much of the information necessary for this evaluation comes from analysis of the patients' blood. Blood samples can be taken from both arteries and veins. Arterial blood can be sampled either by placing an arterial catheter or cannula in the patient, or by performing an arterial puncture with a needle. Venous blood can be sampled from a cannula or a venous puncture at the periphery (peripheral venous blood); from a catheter placed in superior venal cava (central venous blood), or from a pulmonary arterial catheter placed in the pulmonary artery (mixed venous blood).

Placements of venous and arterial catheters are invasive procedures and generally restricted to high dependency departments. In addition catheterisation, cannulation or puncture of the arteries instead of the veins increases the risk of complications such as infection, hemorrhage, bleeding, thrombosis, emboli, neurological damage or pseudo-aneurysm formation. Sampling of arterial blood by arterial puncture is generally considered a more difficult procedure than sampling of venous blood through a venous puncture. Consequently, the routine sampling of arterial blood is generally restricted to high dependency environments. In other wards where patients are acutely ommited e.g. cardiology, abdominal surgery, thoracic surgery and medicine, routine sampling of peripheral venous blood is most common.

Many of the measurements taken from the blood, and used to assess the patient state, are similar in the venous and arterial blood samples. These included the electrolytes and such as sodium (Na), potassium (K), the haemoglobin concentration (Hb) and the concentration of abnormal forms of haemoglobin (e.g. carboxyhaemoglobin (COHb), methylhaemoglobin (MetHb)). However, the acid-base status of arterial and venous blood is not the same, regardless of the site of sampling. The acid-base status refers, in general, to the following measurements in blood: the pH, the pressure of oxygen ($pO_2$), the pressure of carbon dioxide ($pCO_2$), the bicarbonate concentration ($HCO_3$), the concentration of base higher than a reference condition (base excess (BE)), the concentration of bicarbonate at a reference $pCO_2$ (standard bicarbonate SBC), the oxygen pressure ($pO_2$) and the saturation of haemoglobin with oxygen ($SO_2$) with $pO_2$ and $SO_2$ often being referred to as the oxygenation status of blood. The variation in acid-base status between arterial and venous blood is due to oxygen removal from the blood and carbon dioxide addition due to metabolism at the tissues. In addition in patients with circulatory or metabolic abnormalities, the production of strong acid at the tissues due to anaerobic metabolism may also modify the acid-base status.

The acid-base status of arterial blood is used to assess the patients' respiratory and metabolic state. It has been argued (Adrogue et al., 1989a, 1989b; Brandi et al., 1995; Radiometer 1997) and to a large extent clinically accepted that venous blood samples are not adequate for assessing the acid/base and respiratory state of patients. This is thought to be particularly true for peripheral venous samples which "are not recommended for blood gas analysis as they provide little or no information on the general status of the patient" (Radiometer 1997).

In the intensive care unit placement of arterial catheters is routine practice and an assessment of the acid-base status can be obtained from the arterial blood. In some other hospital departments e.g. pulmonary medicine, or nephrology, arterial blood gases are also measured. However in other wards admitting acutely ill patients, e.g. cardiology, abdominal surgery, thoracic surgery and medicine, arterial samples are not usually taken. Usually a peripheral venous sample is taken and analysed in a central laboratory. The sample is usually taken aerobically, i.e. no attempt is made to ensure that $pO_2$ and $pCO_2$ remain constant during the sample procedure. Only a small amount of information concerning the acid-base status of the patient is measured in this sample i.e. the standard bicarbonate, $SBC_v$, and haemoglobin $Hb_v$. Other acid base parameters $pH_v$, carbon dioxide pressure ($pCO_{2v}$), base excess ($BE_v$), oxygen saturation ($SO_{2v}$) and oxygen pressure ($PO_{2v}$) are not measured, and if measured would probably not reflect the true values of venous blood at this sample site given the aerobic nature of the sample.

U.S. Pat. No. 6,334,065 describes a pulse oximeter providing simultaneous and non-invasive oxygen status at multiple sites of a patient. The pulse oximeter described measures both arterial and venous oxygen saturation at any specific tissue site of the patient. It is mentioned that a corresponding computation of arterial minus venous oxygen saturation is advantageous for oxygen therapy patients. However, also as mentioned, the pulse oximeter is purely noninvasive in its way of functioning limiting the values capable of being derived.

U.S. Pat. No. 3,874,850 describes an apparatus being an automatic blood sample analyzer for automatically measuring one or more unknown data or parameters of the blood samples.

Based on the values measured, the apparatus comprises means for calculating a number of other parameters including acid-base status of the blood sample. The analyzer may also comprise means for photo-metrically measuring the hemoglobin contents of samples of blood. There is no computation of arterial blood values based on venous blood samples.

SUMMARY OF THE INVENTION

The object of the invention is to provide a method for performing the conversion of venous blood values to arterial values, including the design of a sampling tube for sampling anaerobic venous blood and including a system for applying the method.

This object may be obtained by a method comprising the steps of:
a) measuring arterial oxygenation,
b) measuring and estimating values of venous blood acid/base status and oxygenation status of a venous blood sample taken anaerobically,
c) converting the venous blood values by applying a mathematical model for deriving blood acid/base status and oxygenation status into estimated arterial blood values.

The object may also be obtained by a method comprising the steps of:
a) estimating arterial oxygenation,
b) measuring and estimating values of venous blood acid/base status and oxygenation status of a venous blood sample taken anaerobically, c) converting the venous blood values by applying a mathematical model for deriving blood acid/base status and oxygenation status into estimated arterial blood values.

The object may also be obtained by a method comprising the steps of:
- b) measuring and estimating values of venous blood acid/base status and oxygenation status of a venous blood sample taken anaerobically,
- a) measuring arterial oxygenation,
- c) converting the venous blood values by applying a mathematical model for deriving blood acid/base status and oxygenation status into estimated arterial blood values.

The object may also be obtained by a method comprising the steps of:
- b) measuring and estimating values of venous blood acid/base status and oxygenation status of a venous blood sample taken anaerobically,
- a) estimating arterial oxygenation,
- c) converting the venous blood values by applying a mathematical model for deriving blood acid/base status and oxygenation status into estimated arterial blood values.

The only differences between the above four methods are the order, in which the different steps are carried out and that the arterial oxygenation may either be measured or estimated. Additionally, both a measurement and an estimation may be performed.

By means of mathematical models for the acid-base status of the body, venous blood sample values of acid-base status and of oxygen status together with pulse oximetry may be used to convert the venous blood values to corresponding arterial values. Deriving of blood acid/base status and oxygenation status into estimated arterial blood values may be performed either by estimation, or by calculation or by a combination of estimation and calculation.

We argue that parameters describing the venous acid-base chemistry should be measured, and describe a method whereby venous values can be combined with a determination of arterial oxygen saturation with a pulse oximeter to calculate predictions ($SBC_{ap}$, $PH_{ap}$, $pCO_{2ap}$, $BE_{ap}$, $pO_{2ap}$, and $SO_{2ap}$) of the corresponding arterial values, ($SBC_a$, $pH_a$, $pCO_{2a}$, $BE_{pO2a}$, and $SO_{2a}$). This implies that the acid/base and respiratory status can be assessed without taking an arterial blood sample. To do so requires anaerobic sampling of the venous blood and this patent also describes the design of a sampling bottle for this purpose. This method will make acid/base and respiratory status available in a large number of patients without the cost, risk and inconvenience of taking an arterial sample, in particular in departments where arterial samples traditionally are only taken rarely. Having the acid/base and respiratory status available will make it easier to diagnose different types of respiratory and metabolic acidosis or alkalosis.

The assumptions of the models comprise that no acid is added between the arterial blood and the venous blood drawn, i.e. no anaerobic metabolism is taking place in the intermediate organ or tissue. It is known that this is not the case for haemo-dynamically unstable patients and for patients with severe chronic suffering.

In a first possible improved method, said measuring and analyzing comprises the further steps of:
- d) drawing an anaerobic venous blood sample,
- e) analysing said anaerobic venous blood sample for evaluating the acid/base status of the venous blood sample, and
- f) analysing said anaerobic venous blood sample for evaluating the oxygenation status of the venous blood sample.

In another possible improved method, said measuring and analyzing comprises the further steps of:
- d) drawing an anaerobic venous blood sample,
- f) analysing said anaerobic venous blood sample for evaluating the oxygenation status of the venous blood sample, and
- e) analysing said anaerobic venous blood sample for evaluating the acid/base status of the venous blood sample.

The only difference between the above two improved methods is the order in comparison with step d), in which the two other steps, i.e. step e) and step f), are carried out.

In a possible further improved method, said method comprises the further step of:
- g1) measuring the arterial oxygenation such as oxygen saturation, pressure or concentration by applying any suitable means for such measuring or estimation, said further step being performed at any time in relation to any of the steps of claims 1-3.

In another further improved method, said method comprises the further step of:
- g2) estimating the arterial oxygenation such as oxygen saturation, pressure or concentration by applying any suitable means for such measuring or estimation, said further step being performed at any time in relation to any of the steps of claims 1-3.

The only difference between the above two further improved methods is the arterial oxygenation either being measured or estimated. Additionally, both a measurement and an estimation may be performed, i.e. step g2) being performed additional to step g1).

In an even further improved method, said method comprises the even further step of
- h) simulating the blood acid/base status and oxygenation status of an arterial blood sample by use of mathematical modelling. Additional hereto, the method may be still even further improved by said method comprising the still even further steps of:
- i) mathematical modelling comprising simulated addition of oxygen, $O_2$, to and removal of carbon dioxide, $CO_2$, from the venous blood sample values in a ratio determined by the respiratory quotient,
- j) said mathematical modelling being performed until the simulated oxygen level is equal to the arterial oxygenation level measured or estimated, and
- k1) calculating the acid/base status and the oxygenation of the arterial blood by applying the result of said modelling, and alternative or additional hereto, said method comprising the still even further steps of
- i) mathematical modelling comprising simulated addition of oxygen, $O_2$, to and removal of carbon dioxide, $CO_2$, from the venous blood sample values in a ratio determined by the respiratory quotient,
- j) said mathematical modelling being performed until the simulated oxygen level is equal to the arterial oxygenation level measured or estimated, and
- k2) estimating the acid/base status and the oxygenation of the arterial blood by applying the result of said modelling.

The only difference between the above two further improved methods is the acid/base status and the arterial oxygenation either being measured or estimated. Additionally, both a measurement and an estimation may be performed, i.e. step k2) being performed additional to step k1).

In an additional possible improved method, said method comprises a further step of l1) measuring the arterial carbon dioxide level such as carbon dioxide pressure, total concentration or bicarbonate concentration) by applying any suitable means for such measuring or estimation, said further step being performed at any time in relation to any of the steps of claims 1-6.

In another additional improved method, said method comprises a further step of 12) estimating the arterial carbon dioxide level such as carbon dioxide pressure, total concentration or bicarbonate concentration) by applying any suitable means for such measuring or estimation, said further step being performed at any time in relation to any of the steps of claims 1-6.

The only difference between the above two further improved methods is that arterial carbon dioxide level may either be measured or estimated. Additionally, both a measurement and an estimation may be performed, i.e. step 12) being performed additional to step 11).

In a possible further improved method, said method comprises an even further step of m) simulating the blood acid/base status and oxygenation status of arterial blood sample by use of modelling. Additional hereto, the method may be still event further improved by said method comprising the still even further steps of:

n) mathematical modelling comprising simulated addition of $O_2$ to and removing $CO_2$ from the venous blood sample values in a ratio determined by the respiratory quotient, o) said modelling being performed until the simulated carbon dioxide level is equal to the arterial carbon dioxide level measured or estimated, and p1) calculating the acid/base status and the oxygenation of the arterial blood by applying the result of said modelling.

And alternative or additional hereto, said method comprising the still even further steps of n) mathematical modelling comprising simulated addition of $O_2$ to and removing $CO_2$ from the venous blood sample values in a ratio determined by the respiratory quotient, o) said modelling being performed until the simulated carbon dioxide level is equal to the arterial carbon dioxide level measured or estimated, and p2) estimating the acid/base status and the oxygenation of the arterial blood by applying the result of said modelling.

The only difference between the above two further improved methods is the acid/base status and the arterial oxygenation either being measured or estimated. Additionally, both a measurement and an estimation may be performed, i.e. step p2) being performed additional to step p1).

The potential for use of venous blood samples to assess the status of acutely ill patients in various hospital departments is illustrated in FIG. 1 which graphically shows the acute blood samples in different patient groups at Aalborg Hospital in Denmark in 1999. Light bars indicate arterial blood samples, dark bars indicate venous blood samples. Three different types of department can be identified within those treating acutely ill patients. In the first group arterial blood samples are taken frequently (70,000 per year at Aalborg Hospital, Denmark) (the population of Aalborg is approximately 160,000) and often analysed at the point of care. This group includes intensive care units, departments of anaesthesia and trauma units. In the second group arterial blood samples are taken regularly (2,000 arterial blood samples per year at Aalborg Hospital, Denmark). This group includes the departments of pulmonary medicine and nephrology. In the third group arterial blood samples are taken occasionally. This group includes for example departments of cardiology, abdominal surgery, thoracic surgery and medicine.

In the departments of groups 2 and 3 venous blood samples are taken much more frequently than arterial samples. Indeed, when taken in total, the number of venous blood samples taken in acutely ill patients actually exceeds the number of arterial blood samples (FIG. 1). It is in these departments that venous samples are usually analysed in the central laboratory where measurements of standard bicarbonate (SBC), total haemoglobin (Hb), and other blood values are taken, without a full blood gas analysis.

In order to test the strength and validity of the models it is therefore necessary to test the models for different groups of patients with varying haemo-dynamic conditions and accordingly different $O_2$ and $CO_2$ conversion in the tissues.

Input for the mathematical models are venous values together with information of the arterial oxygenation as measured by means of as example a pulse oximeter.

In order to verify the validity of the models for converting venous blood sample values to arterial values the corresponding arterial values derived may be compared to an arterial blood sample drawn simultaneously with drawing of the venous blood sample.

BRIEF DESCRIPTION OF THE DRAWINGS

FIG. 6 illustrates a Bland-Altman plot of measured arterial carbon dioxide pressure pCO 2 ($pCO_{2,a}$) versus that predicted using the venous to arterial conversion method ($pCO_{2,ap}$). FIG. 7 is a Bland-Altman plot of measured arterial Standard Bicarbonate SBC ($SBC_a$) versus that predicted using the venous-to-arterial conversion method ($SBC_{ap}$), while FIG. 8 is a Bland-Altman plot of measured arterial Base Excess BE($BE_a$) against that predicted from the arterial-to-venous conversion method ($BE_{ap}$), where $BE_a$-$BE_{ap}$=0.2. FIG. 9 illustrates a Bland-Altman plot of measured arterial pH ($PH_a$) versus that predicted using the venous-to-arterial conversion method ($PH_{ap}$).

DESCRIPTION OF THE INVENTION

Figure 1:
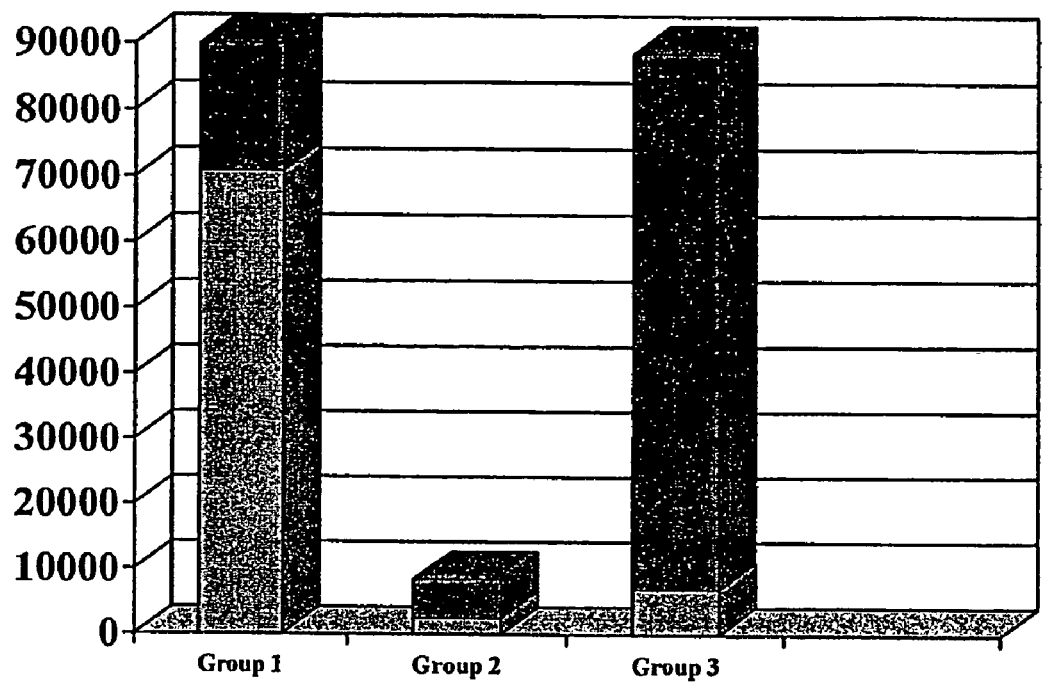
FIG. 1 provides a graphical representation of the use of venous blood samples from different patient groups to assess patient status in various departments of a hospital.
Figure 2:
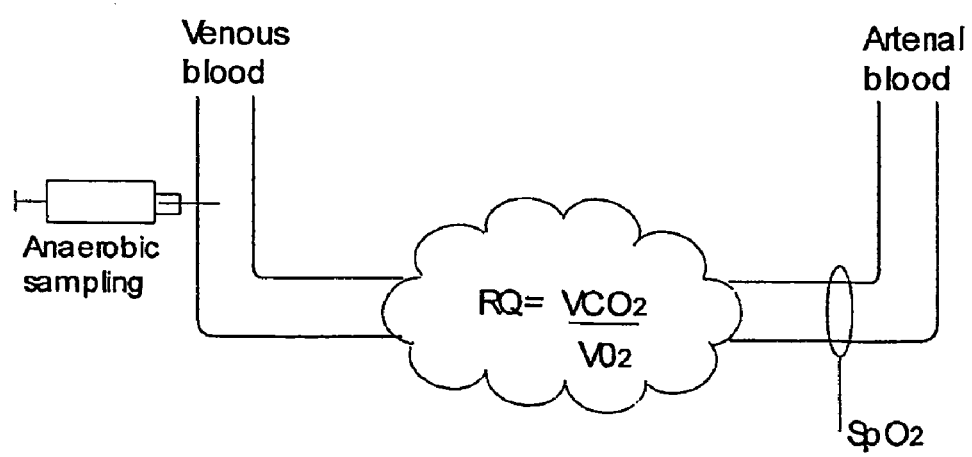
FIG. 2 is a schematic representation of methodology for predicting arterial values from a venous blood sample.

This section will be described in four parts. In part 1 the invention will be described with reference to the accompanying FIG. 2 schematically showing a method for performing the prediction of arterial values from a venous blood sample.

In part 2 a design for a sampling bottle, capable of being used for anaerobic sampling of venous blood, is described. Anaerobic venous samples being required for the method described in step 1 (see part 1).

In part 3 two patient cases are described, both illustrating the potential use of the method. The first patient had a metabolic alkalosis due to potassium deficiency. In that patient a venous blood sample converted to arterial values would have revealed this problem before it developed into a crisis. The second example is a postoperative patient, where an arterial sample was actually available. This case is included to show that the information that can be derived from a venous sample converted into arterial values is equivalent to the information derived from the arterial sample. The case also shows that conversion of venous blood to arterial values is necessary: the calculated arterial values showed that arterial $pCO_2$ was normal, despite the high venous value.

In part 4 it is shown that arterial values, calculated from the method of converting venous to arterial values, compare well with measured arterial values in 69 patient cases, including some categories of very ill patients. The accuracy of the converted venous values does not match what is obtained from an arterial sample, but is clearly sufficient for a clinical judgement to be made. As a minimum the arterialization method can be seen as a quite accurate screening method, that indicates when an arterial sample should be taken.

Part 1. Conversion of Venous Blood Values to Arterial Blood

The invention will be described with reference to the accompanying FIG. 2 schematically showing a method for performing the prediction of arterial blood acid-base status values from an anaerobically sampled venous blood sample.

Arterial blood gasses are, as an example, estimated as given in the 4 steps below.

Step 1: An anaerobic venous blood sample is drawn and analysed using standard blood gas analysis technology (e.g. Radiometer, 1994) to provide a picture of the acid/base status of the venous blood ($SBC_v$, $pH_v$, $pCO_{2v}$, $BE_v$, $pO_{2v}$ and $SO_{2v}$).

Step 2: The arterial oxygen saturation is estimated or measured non-invasively, possibly by pulse oximetry.

Step 3: For a blood sample passing through the tissues from the arteries into the veins, the ratio of the amount of $CO_2$ added (i.e. the rate of $CO_2$ production ($VCO_2$)) and $O_2$ removed (i.e. the rate of $O_2$ utilisation ($VO_2$)), due to aerobic metabolism is defined as the respiratory quotient ($RQ=VCO_2/VO_2$). RQ is often approximated by measurement of inspiratory and expiratory gases taken at the mouth, through the measurement of inspiratory oxygen ($FIO_2$) and carbon dioxide ($FiCO_2$) fraction and either end tidal fractions of oxygen ($Fe'O_2$) and carbon dioxide ($Fe'CO_2$) or mixed expired fractions of oxygen ($FeO_2$) and carbon dioxide ($FeCO_2$) using the equations:

$$RQ = \frac{Fe'CO_2 - FiCO_2}{FiO_2 - Fe'O_2} \text{ or } RQ = \frac{FeCO_2 - FiCO_2}{FiO_2 - FeO_2}$$

Approximation of RQ by this method often gives values which can vary substantially. However, the true value of RQ at the tissues can only vary between 0.7-1.0, being 0.7 In aerobic metaboism of fat and 1.0 in aerobic metabolism of carbohydrate. In this step a mathematical model of blood acid/base and oxygenation status (e.g. Rees et al, 1996, 1997) is used to perform a simulation, where $O_2$ is added and $CO_2$ removed from the venous blood in a ratio determined by a constant respiratory quotient, set to be within the physiologically possible range 0.7-1.0. This simulation is performed until the simulated oxygen saturation is equal to that estimated or measured in step 2, i.e. that in arterial blood.

Step 4: The model of blood acid/base and oxygenation status is then used to calculate a picture of the acid/base status and the oxygenation of the arterial blood ($SBC_{ap}$, $pH_{ap}$, $pCO_{2ap}$, $BE_{ap}$, $pO_{2ap}$ and $SO_{2ap}$). This is possible as the simulated removal of $CO_2$ and $O_2$ from venous blood at a fixed RQ ensures that when the simulated arterial oxygenation matches that measured, then the simulated values of other arterial acid-base variables should also match those measured.

For the purpose of testing the venous to arterial conversion method the predictions of arterial acid base status ($SBC_{ap}$, $pH_{ap}$, $pCO_{2ap}$, $BE_{ap}$, $pO_{2ap}$ and $SO_{2ap}$) obtained from the method can be compared against those measured ($SBC_a$, $pH_a$, $pCO_{2a}$, $BE_a$, $pO_{2a}$ and $SO_{2a}$), examples of which are given in sections 3 and 4.

The fundamental assumption contained in this method is that little or no anaerobic metabolism occurs across the tissue where the venous blood sample is taken. If anaerobic metabolism were present then this would result in two effects, the base excess in the arterial and venous blood would be different, and the strong acid produced by this process ($H^+$) would bind with bicarbonate ($HCO3^-$) in the blood to form $CO_2$ In the following reversible reaction $$H^+ + HCO_3^- \leftrightarrow CO_2 + H_2O$$

The increase in $CO_2$ production by this reaction would mean that the apparent $VCO_2$ would be increased without an increase in $VO_2$, meaning that conversion of venous values to arterial values using a constant RQ would not be correct. The degree of anaerobic metabolism depends upon the circulatory and metabolic state of the patient. In a normal well perfused peripheral limb it is unlikely that anaerobic metabolism occurs. The quality of perfusion of a limb can be assessed clinically by the presence of a clearly recognizable arterial pulse determined by palpation, a normal capillary response, and a normal color and temperature of the limb. Central or mixed venous blood is a mixture of blood from several sites and may therefore contain blood from an area of the body with anaerobic metabolism. The selection of the sample site is therefore important. In section 3 the validity of the method is tested for peripheral venous blood sampled from a clinically considered well perfused arm by comparing arterial values derived using the method with those obtained from an arterial blood sample drawn simultaneously with the drawing of the venous sample.

Part 2. Design of a Sampling Bottle, Capable of Being used for Anaerobic Sampling of Venous Blood.

The method of converting venous values describing the acid-base status of the blood to arterial values only applies if the venous blood samples are taken anerobically, i.e. It is ensured that the $O_2$ and $CO_2$ pressure in the sample remains constant during and after the sampling procedure.

Figure 3:
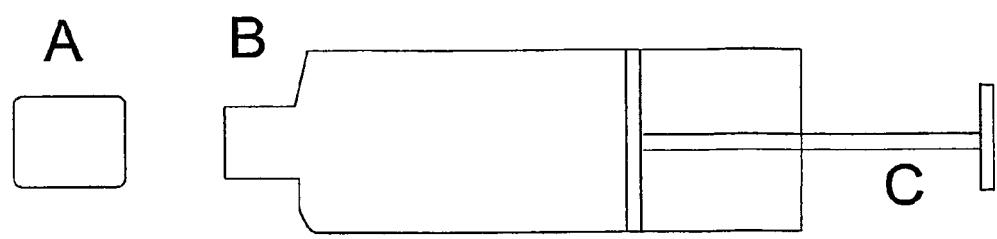
FIG. 3 illustrates schematically a sampling syringe from a sampling connector (A) at the sampling site of an arterial catheter, cannula or needle, by which arterial samples may be taken anaerobically.

Currently, it is normal practice that only arterial samples are taken anaerobically. These are usually taken via a sampling syringe from a sampling connector (A) at the sampling site of an arterial catheter, cannula or needle, as illustrated in FIG. 3. Arterial sampling syringes are heparinized to prevent coagulation of the sample. After sampling of the blood the syringe is usually placed in a verticle position with the open end (B) (FIG. 3) uppermost, agitated and trapped air expelled using the plunger (C). This is only possible because the syringe is open to the environment, a lid being placed on the syringe only after expulsion of trapped air.

Figure 4:
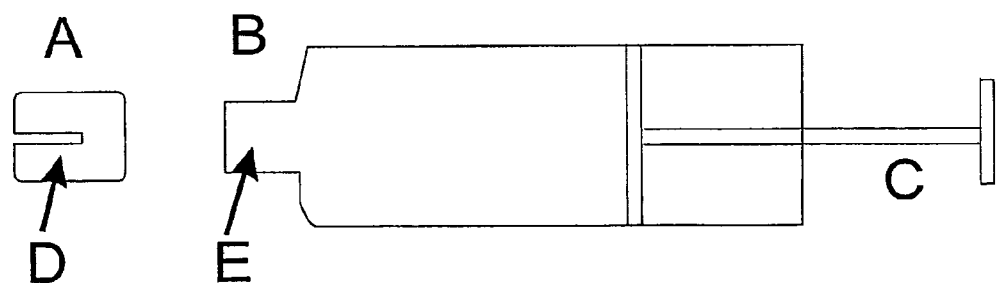
FIG. 4 is a schematic depiction of a sampling syringe for venous blood samples, which usually are not taken via an open syringe.

In principle, venous blood sampled using arterial sampling syringes could be used in the method of converting venous to arterial values described here. However, the use of open syringes increases the risk of infection of the person handling the blood. In departments routinely taking venous blood to assess the status of acutely admitted patients, venous blood samples are not usually taken using open syringes. Instead venous blood samples are taken using the sampling method illustrated in FIG. 4. A venous sampling connector (A) is attached to the venous sampling site. The connector includes a needle (D), covered with rubber so as to prevent leakage of blood except when pressure is applied to the rubber to expose the needle. The venous sampling bottle is sealed with a sealing membrane (E). Blood cannot enter or leave the bottle until the bottle is pressed onto the sampling connector. At this point the needle is exposed, pierces the sealing membrane, and a blood sample may be taken. Different sampling bottles often contain chemicals for specific conservation or analysis of the blood depending upon the parameters to be measured e.g. electrolytes, coagulation etc. However these sampling bottles also contain oxygen and/or carbon dioxide (typically air), which may diffuse into the blood sample altering its acid base status. In addition, since the sample bottle is closed there is no means to expel air which may enter the bottle during the sampling procedure.

Figure 5:
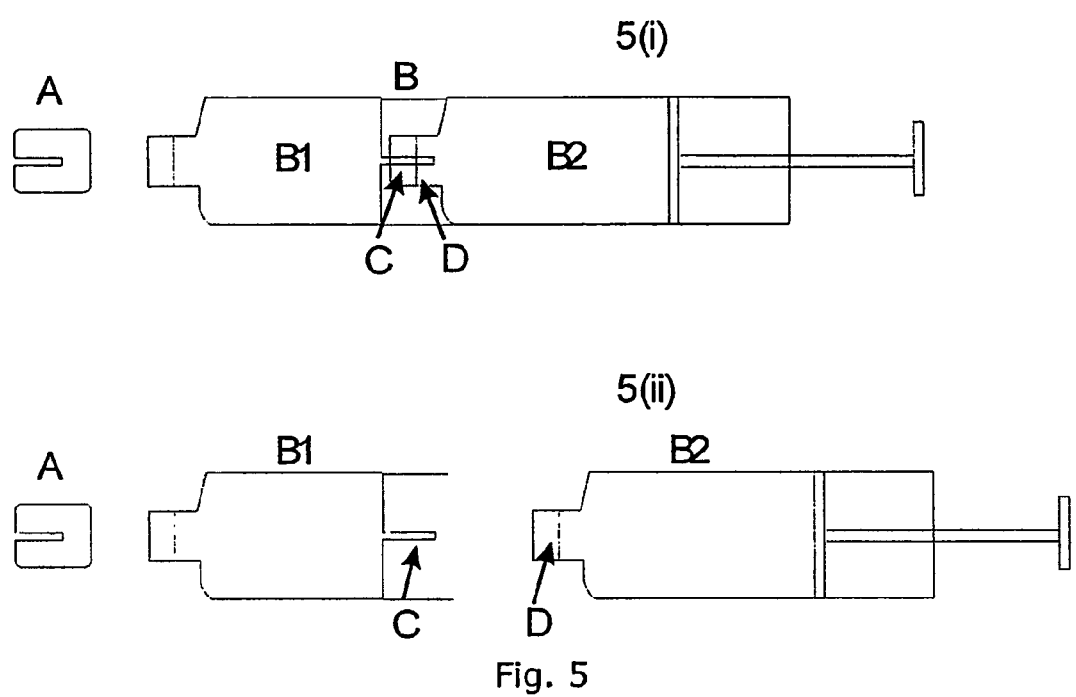
FIG. 5 illustrates schematically the design of a sample bottle of the invention, suitable for anaerobic sampling of venous blood.

FIG. 5 illustrates an example of the invention according to claims 17-20 i.e. the design of a sample bottle suitable for anaerobic sampling of venous blood.

The example design illustrates a sample bottle (B) with two heparinized chambers B1 and B2. Initially the two chambers are joined, as illustrated in FIG. 5(*i*). The complete bottle is then pressed on the sampling connector (A) and the plunger used to draw blood, and possibly air into both compartments. The sample bottle is then detached from the sampling connector as illustrated in FIG. 5(*ii*) b and placed vertically with the plunger facing uppermost. By agitating the bottle and withdrawing the plunger further, any air in chamber B1 is drawn into chamber B2. The two chambers B1 and B2 are then separated. The rubber seals on the sampling needle (C) and the sealing membrane (D) ensure no leakage of blood. Chamber B1 contains only anaerobic venous blood, analysis of which may then be used in the arterial conversion algorithm. Chamber B2 contains air and blood and may be discarded.

The amount of air in the chambers can be further reduced by applying a partial or complete vacuum within the sample bottle prior to sampling. In addition if the initial gas in the sampling bottle contains inert gasses, and or $O_2$ and $CO_2$ with pressures adjusted to typical venous values, then the effects of any residual gasses in the sampling bottle will be minimised.

Part 3. Clinical Cases Illustrating the Potential Use of the Venous to Arterial Conversion Method This section describes two patient examples, the first with a metabolic alkalosis due to potassium deficiency. In this patient a venous blood sample converted to an arterial value would have revealed the problem before it developed into a crisis. The second example is a postoperative patient, where an arterial sample was actually available. This case is included to show that the information that can be derived from an venous sample converted to arterial values is equivalent to the information derived from the arterial sample. The case also shows that conversion of venous values to arterial values is necessary: the converted venous values show that arterial $pCO_2$ is normal, despite the high venous value.

Case 1—Metabolic Alkalosis due to Potassium Deficiency

A patient, age 60, male, was acutely admitted to the surgical department complaining of abdominal pain, and having vomited repeatedly over the past week. A peripheral venous sample was taken and analysed routinely, without a blood gas analysis, giving a high standard bicarbonate $SBC_v=38$ mmol/l, a slightly low haemoglobin $Hb_v=7.0$ mmol/l, and a potassium value at the low end of the normal range $K_v=3.6$ mmol/l. The high SBC caused by loss of acid and potassium due to vomiting remained unnoticed for 3 days, at which point the patients respiratory drive and cardiac function had deteriorated to the point of pulmonary odema, and an arterial blood gas was taken. Arterial blood gas values ($pH_0=7.60$, $BE_a=18$ mmol/l, $pCO_{2,a}=6.0$ kPa, $SO_{2,a}=0.92$) showed very severe metabolic alkalosis. The patient was then transferred to the intensive care unit, where treatment for this metabolic alkalosis proceeded for approximately two weeks.

For this patient, analysis of the peripheral venous blood gases on admission might have highlighted the severe alkalosis. In current clinical practice analysis of the peripheral venous blood gases are not generally accepted (Radiometer 1997). Conversion of the venous blood gas values to arterial values using the method included here might then both have highlighted the severe alkalosis before the patient reached a critical state, and given a clinically acceptable picture of the patient.

Case 2—Post-Operative Coronary Artery Bypass Patient

A patient, age 64, male, presented in the post operative intensive care unit following coronary artery bypass surgery. During the post operative period the patient was heamodynamically stable. An arterial catheter was present in this patient and simultaneous samples of arterial and peripheral venous blood were taken and analysed for blood gases. Venous blood values were $SBC_v=23.7$ mmol/l, $pH_v=7.29$, $pCO_{2,v}=7.2$ kPa, $BE_v=-0.3$ mmol/l and $SO_{2,v}=0.36$. If interpreted directly these values would suggest that the patient had a respiratory abnormality causing a high $pCO_{2,v}$. However, when the venous to arterial conversion method was used to calculate arterial blood gas values a relatively normal pattern presented $SBC_{ap}=22.9$ mmol/l, $pH_{ap}=7.35$ $pCO_{2,ap}$, $=5.8$ kPa, $BE_{ap}=-1.8$ mmol/l and $SO_{2,ap}=0.98$ suggesting that the patient did not have a respiratory abnormality. These converted venous values gave the same clinical picture as arterial values measured for comparison ($SBC_a=23.6$ mmol/l, $pH_{ap}=7.37$, $pCO_{2,a}=5.8$ kPa, $BE_{ap}=-1.8$'$-1.1$ mmol/l, and $SO_{2,ap}=0.98$), which were also within the normal range. The information derived from the converted venous sample was therefore clinically equivalent to the information derived from the arterial sample. In this case an interpretation of the patient state could not be made from the venous blood without a conversion to arterial values since the converted values showed that arterial $pCO_2$ was normal, despite the high venous value. If this patient had presented at the ward, without an arterial catheter conversion of venous blood to arterial values would have been necessary to obtain the correct clinical interpretation.

Part 4. Conversion of Venous Blood Values to Arterial Values in 69 Clinical Cases This section describes the results of using the method for conversion of venous to arterial values. Peripheral venous blood samples were taken in 69 cases, and used to measure $SBC_v$, $pH_v$, $pCO_{2,v}$, $BE_v$, $pO_{2,v}$ and $SO_{2,v}$. The method was then used to predict arterial blood values $SBC_{ap}$, $pH_{ap}$, $pCO_{2,ap}$, $BE_{ap}$, $pO_{2,vap}$ and $SO_{2,ap}$. These arterial predictions were then compared with measurements of arterial blood $SBC_a$, $pH_a$, $pCO_{2,a}$, $BE_a$ and $SO_{2,a}$ taken simultaneously with the venous samples. Section 4.1 describes the patient groups included in this study including their severity of metabolic and respiratory disorders. Section 4.2 describes the results of the venous to arterial conversion method. In this section predicted variables ($SBC_{ap}$, $pH_{ap}$, $pCO_{2,ap}$, $BE_{ap}$ and $SO_{2,ap}$) are compared in turn to measured arterial values, and the accuracy and precision of the prediction quantified. FIGS. 6 through 9 illustrate Bland-Altman plots illustrating the mean of the measured and predicted arterial value plotted against the difference between the measured and predicted arterial values. Values of the mean difference between measured and predicted arterial values and the standard deviation, are also given in graphs 6-9 and in the following text.

4.1 Study Population

Patients were studied from the following groups a) post operative coronary artery bypass patients, both haemodynamically stable and unstable; b) patients with sepsis, both haemodynamically stable and unstable; and d) Patients with chronic obstructive lung disease, both mechanically ventilated and spontaneously breathing. These groups were selected to represent a range of acid base status including metabolic and respiratory abnormalities, and presented with the values (median, range) pH, =7.40, 7.24 to 7.54; $BE_a$=0.6 mmol/l, −6.9 to 19.7 mmol/l; SBC, =25.0 mmol/l, 18.8 to 44.3 mmol/l; $pCO_{2,a}$=5.68 kPa, 4.0 to 10.8 kPa. Patients also presented with a broad range of arterio-venous oxygen saturation difference (median, range) 0.15, 0.00 to 0.74. Arterial and peripheral venous blood samples were taken simultaneously with peripheral samples being taken from what were clinically considered well perfused arms. Results of these groups are presented here pooled.

4.2 Results

In this section we present a comparison of arterial values predicted using the venous to arterial conversion method ($SBC_{ap}$, $pH_{ap}$, $PCO_{2,ap}$, $BE_{ap}$ and $SO_{2,ap}$) with measured arterial values ($SBC_a$, $pH_a$, $pCO_{2,a}$, $BE_a$, and $SO_{2,a}$).

$pCO_{2,a}$ versus $pCO_{2,ap}$

Figure 6:
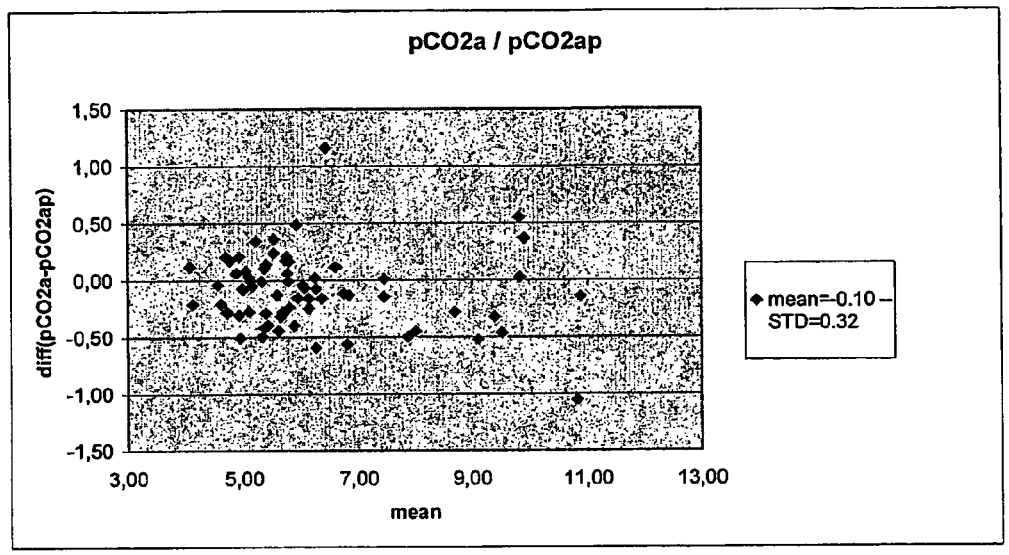
FIGS. 6 through 9 present Bland-Altman plots that depict the mean of measured and predicted arterial value plotted against the difference between the measured and predicted arterial values. Thus.

FIG. 6 Illustrates a Bland-Altman plot of measured arterial carbon dioxide pressure pCO2 ($pCO_{2,a}$) versus that predicted using the venous to arterial conversion method ($pCO_{2,ap}$). The prediction of $PCO_{2ap}$ can be seen as both accurate and precise ($pCO_{2,a}-pCO_{2,ap}$=−0.10∀0.32 kPa). In addition, errors in the prediction of $pCO_{2,ap}$ are clinically unimportant when compared to the size of the arterial—venous $pCO_2$ difference $pCO_{2,a}-pCO_{2,v}$=−0.64∀0.63 kPa.

$SBC_a$ verus $SBC_{ap}$

Figure 7:
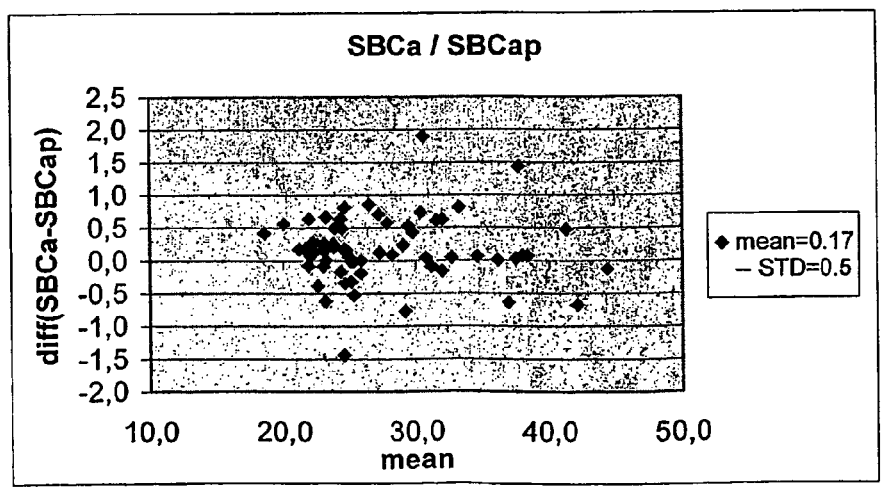

FIG. 7 illustrates a Bland-Altman plot of measured arterial Standard Bicarbonate SBC ($SBC_a$) versus that predicted using the venous to arterial conversion method ($SBC_{ap}$). The prediction of $SBC_{ap}$ can be seen as both accurate and precise ($SBC_a-SBC_{AP}$=0.17∀0.5 mmol/l). Since SBC changes with the addition of acid, the small bias of 0.17 mmol/l is equivalent to the finding that the base excess changes by about 0.2 mmol/i as the blood flows through the tissues.

$ABE_a$ versus $ABE_{ap}$

Figure 8:
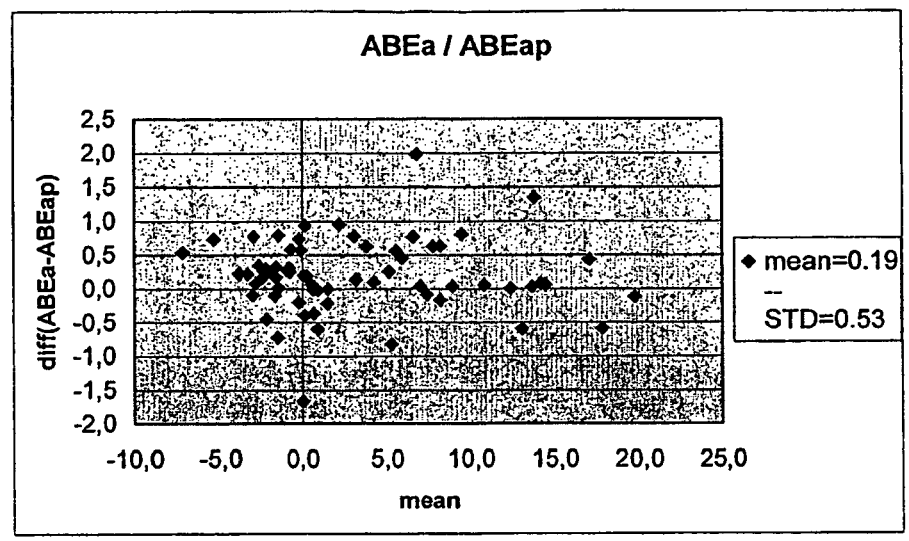

The major assumption in the venous to arterial conversion method is that no significant amount of strong acid is added to the blood as it passes through the tissues across which the arterial and venous blood samples are taken. To verify this, FIG. 8 Illustrates a Bland-Altman plot of measured arterial Base Excess BE ($BE_a$) against that predicted from the arterial to venous conversion method ($BE_{ap}$). $BE_a-BE_{ap}$=0.2∀0.5 mmol/l. This implies that 0.2∀0.5 mmol/l acid is added when the blood is passing through the tissues i.e an Insignificant amount.

$PH_a$ versus $pH_{ap}$

Figure 9:
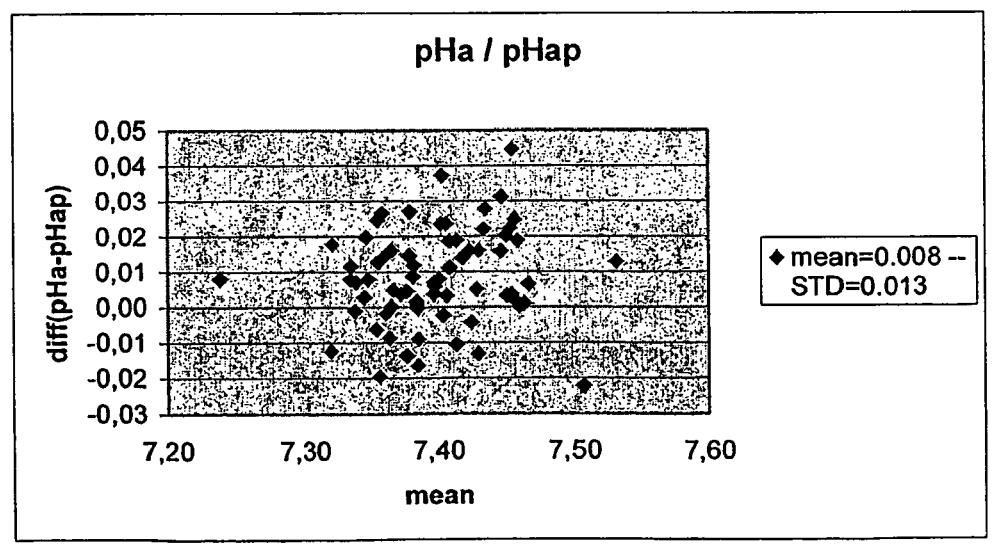

FIG. 9 illustrates a Bland-Altman plot of measured arterial pH ($pH_a$) versus that predicted using the venous to arterial conversion method ($pH_{ap}$). The prediction of $pH_{ap}$ can be seen as both accurate and precise ($pH_a-pH_{ap}$=0.008∀0.013).

Possible Groups of Patients Suitable for the Invention.

The patient groups presented in section 4 reflect the testing of the method where simultaneous sampling of arterial blood is necessary for comparison with the those calculated by the method. When applying the method arterial samples would not be taken. The method may therefore be applied in all: normal subjects, patients, or animals in which a venous sample can be taken in combination with a measurement of arterial oxygenation, usually performed using a pulse oximeter. Whilst the method is tested here for the sampling of peripheral venous blood the method may also be applied to the sampling of central or mixed venous blood.

REFERENCE LIST

1. Rees S E, Andreassen S., Hovorka R, Summers R, Carson E R: Acid-base chemistry of the blood—a general model. Comput. Methods Programs Blomed. 1996; 51: 107-19
2. Rees S. E., S. Andreassen, R Hovorka and E. R. Carson: A dynamic model of carbon dioxide transport in the blood. In: D. Linkens and E. R. Carson (Eds). Proceedings of the 3rd International Federation of Automatic Control (IFAC) symposium on Modelling and Control in Biomedical Systems, Elsevier, December 1997, pp 63-68.
3. Adrogue H J, Rashad M N, Gorin A B, Yacoub J, Madias N E: Assessing acid-base status in circulatory failure. Differences between arterial and central venous blood. N. Engl. J. Med. 1989; 320: 1312-6
4. Brandi L S, Glunta F, Pieri M, Sironi A M, Mazzanti T: Venous-arterial PCO2 and pH gradients in acutely ill post-surgical patients. Minerva Anestesiol. 1995; 61: 345-50
5. Radiometer Medical A/S: The Blood gas Handbook, 1997, pp 14-15
6. Radiometer Medical A/S: Blood Gas, Oximetry and Electrolyte Systems. Reference Manuel, 1994

The invention claimed is:

1. A method of converting venous blood values to arterial blood values, said method comprising the steps of:
   a) providing values of arterial oxygenation,
   b) measuring and estimating values of acid/base status and oxygenation status in a blood sample, the sample being obtained from peripheral venous blood,
   c) converting the venous blood values by applying a mathematical model for deriving blood acid/base status and oxygenation status into estimated arterial blood values.

2. A method according claim 1, said method measuring and analyzing comprising the further steps of:
   d) providing an anaerobic venous blood sample obtained from peripheral venous blood,
   e) analyzing said anaerobic venous blood sample for evaluating the acid/base status of the venous blood sample, and
   f) analyzing said anaerobic venous blood sample for evaluating the oxygenation status of the venous blood sample.

3. A method according to claim 1, said method comprising the further step of:
   g) providing the arterial oxygenation such as oxygen saturation, pressure or concentration, said further step being performed at any time in relation to any of the steps a)-c).

4. A method according to claim 3, said method comprising the even further step of:
   h) simulating the blood acid/base status and oxygenation status of an arterial blood sample by use of mathematical modelling.

5. A method according to claim 4, said method comprising still even further steps of i) mathematical modelling comprising simulated addition of oxygen, $O_2$, to and removal of carbon dioxide, $CO_2$, from the venous blood sample values in a ratio determined by the respiratory quotient, j) said mathematical modelling being performed until the simulated oxygen level is equal to the arterial oxygenation level measured or estimated, and k1) calculating the acid/base status and the oxygenation of the arterial blood by applying the result of said modelling.

6. A method according to claim 5, said method comprising still even further steps of i) mathematical modelling comprising simulated addition of oxygen, $O_2$, to and removal of carbon dioxide, $CO_2$, from the venous blood sample values in a ratio determined by the respiratory quotient, j) said mathematical modelling being performed until the simulated oxygen level is equal to the arterial oxygenation level measured or estimated, and k2) estimating the acid/base status and the oxygenation of the arterial blood by applying the result of said modelling.

7. A method according to claim 1, said method comprising a further step of l) providing the arterial carbon dioxide level such as carbon dioxide pressure, total concentration or bicarbonate concentration said further step being performed at any time in relation to any of the steps a)-c).

8. A method according to claim 7, said method comprising an even further step of m) simulating the blood acid/base status and oxygenation status of arterial blood sample by use of modelling.

9. A method according to claim 8, said method comprising the still even further steps of n) mathematical modelling comprising simulated addition of $O_2$ to and removing $CO_2$ from the venous blood sample values in a ratio determined by the respiratory quotient, o) said modelling being performed until the simulated carbon dioxide level is equal to the arterial carbon dioxide level measured or estimated, and p1) calculating the acid/base status and the oxygenation of the arterial blood by applying the result of said modelling.

10. A method according to claim 8, said method comprising the still even further steps of n) mathematical modelling comprising simulated addition of $O_2$ to and removing $CO_2$ from the venous blood sample values in a ratio determined by the respiratory quotient, o) said modelling being performed until the simulated carbon dioxide level is equal to the arterial carbon dioxide level measured or estimated, and p2) estimating the acid/base status and the oxygenation of the arterial blood by applying the result of said modelling.

11. A method according to claim 10 where the measuring or estimating of the arterial oxygen saturation is done by pulse oximetry.

* * * * *